United States Patent
Becher

(10) Patent No.: US 6,853,395 B1
(45) Date of Patent: Feb. 8, 2005

(54) PROCESS AND DEVICE FOR INSCRIPTION OF A SHEET-LIKE ADHESIVE SYSTEM OF A POLYMER, ESPECIALLY OF A TRANSDERMAL THERAPEUTIC SYSTEM

(75) Inventor: Frank Becher, Koblenz (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 0 days.

(21) Appl. No.: 09/980,917

(22) PCT Filed: Apr. 8, 2000

(86) PCT No.: PCT/EP00/03152

§ 371 (c)(1),
(2), (4) Date: Feb. 20, 2002

(87) PCT Pub. No.: WO00/64684

PCT Pub. Date: Nov. 2, 2000

(30) Foreign Application Priority Data

Apr. 23, 1999 (DE) .......................................... 199 18 473

(51) Int. Cl.⁷ .............................. B41J 2/47; B23K 26/08
(52) U.S. Cl. .................................. 347/225; 219/121.78
(58) Field of Search ................................ 347/224, 225, 347/229, 246, 262; 219/121.28, 121.6, 121.61, 121.78, 121.69

(56) References Cited

U.S. PATENT DOCUMENTS 5,151,572 A * 9/1992 Jack ........................ 219/121.69
5,831,661 A * 11/1998 Tabuchi et al. ............. 347/262

FOREIGN PATENT DOCUMENTS

| DE | 42 43 270 A1 | 6/1994 |
| DE | 196 30 478 | 1/1998 |
| DE | 197 11 243 A1 | 10/1998 |
| DE | 197 42 536 A1 | 4/1999 |
| EP | 0 688 678 | 12/1995 |
| EP | 0 987 121 | 3/2000 |
| JP | 620094343 AA | 4/1987 |
| JP | 40284270 AA | 10/1992 |
| WO | WO 9744196 | 11/1997 |
| WO | WO 98/58685 | 12/1998 |

OTHER PUBLICATIONS

"Rechnergesteuerte Laserbeschriftungsgerate", Kunststoffe, DE; Hanser Verlag, Carl; vol. 78, No. 9; Sep. 1, 1988, p. 771.

* cited by examiner

Primary Examiner—Hai Pham
(74) Attorney, Agent, or Firm—D. Peter Hochberg; Sean Mellino; Katherine R. Vieyra

(57) ABSTRACT

A process for inscription of a sheet-like adhesive system of a polymer, preferably on the adhesive-free side thereof, with information is characterized in that the inscription is carried out with the aid of a movably guided laser beam in such a manner that a detrimental influence on the ingredients contained in the system, in particular by heat generated by the laser beam or by detrimental perforation of a backing layer impermeable to ingredients or water vapour, is avoided, and that to this end the intensity and penetration depth of the laser beam is adjusted according to the material properties of the system in such a way that the laser beam does not penetrate far enough to reach an ingredient-containing layer of the system.

12 Claims, No Drawings

PROCESS AND DEVICE FOR INSCRIPTION OF A SHEET-LIKE ADHESIVE SYSTEM OF A POLYMER, ESPECIALLY OF A TRANSDERMAL THERAPEUTIC SYSTEM

BACKGROUND OF THE INVENTION

1. Field of the Invention

The invention relates to a process for inscription of a sheet-like adhesive system of a polymer, preferably on the side averted from the adhesive side, with information, e.g. indications to identify the system as such or the object to which the system is to be adhered.

2. Description of the Related Art

There are many different types of sheet-like adhesive systems of a polymer, such as:

- adhesive films, e.g. (possibly transparent) adhesive films for identification marking of switchboards and technical appliances,
- technical adhesive strips or tapes,
- fixing plasters (e.g. for fixation of bandages) for application on the skin,
- wound plasters with wound dressings,
- plasters with active agents such as antirheumatic plasters for topical application of active agents to the skin,
- plasters with active agents for system application of active agents onto and through the skin, so-called transdermal therapeutic system (TTSs),
- plant protection plasters comprising active agents for application of plant protection agents.

With sheet-like adhesive systems there is a need to apply information relating, for example, to their properties, their use, their intolerances or incompatibilities, storage conditions and useful life-span, as well as, possibly, information relating to special properties of the object to which the system is to be stuck (label functions), preferably on the side which is averted from the adhesive side.

Also in the case of sheet-like adhesive systems such as medical plasters, that is, fixation plasters, wound plasters and, in particular, in the case of dermal/transdermal therapeutic systems comprising active agents, there is a need, and from case to case an indispensable requirement, to identifiably inscribe, and thereby to mark, such plasters according to their use, the kind of active ingredient, the spectrum of activities and side effects, the potential for intolerance, the allergy potential, the storage conditions, the expiry date, as well as according to information on the patients, etc.

With sheet-like systems such as adhesive systems containing active agents for plant protection there is also a need, and from case to case in indispensable requirement, to identifiably inscribe and thereby to mark such plasters according to the kind of active ingredient, their properties, the spectrum of activities and side effects, the potential for intolerances, the storage conditions, their expiry date, as well as according to information on the plants, etc.

The term "inscription" in the following will be understood as a synonym for any kind of identification, thus also including markings, symbols, bar cods, etc.

In the state of the art it is common practice to imprint and mark such adhesive systems employing, for example, a printing technique such as screen printing or tampon printing. This known technology does, however, have a number of disadvantages:

- the printing ink requires time to dry,
- printing ink adheres only for an insufficient duration to the polymer substrate provided for the purpose,
- the pressure applied in the printing process may have a negative effect on the sheet-like adhesive system, the ingredients contained therein such as adhesives, additives such as softeners and enhancers, or on the active agent,
- ink signs on the polymer substrate are easily blurred, especially upon contact with other materials,
- most of the employable printing techniques can be carried out only intermittently, which reduces the rate of production,
- because of the small working width of the printing techniques employed, the printing of the sheet-like adhesive system can not be performed on the broad webs of the adhesive films, but only after the systems have been separated.

Furthermore, ink jet printers are known, to which in part the same disadvantages but also other disadvantages apply:

- the printing ink requires time to dry,
- printing ink adheres only for an insufficient duration to the polymer substrate provided for the purpose,
- ink signs on the polymer substrate are easily blurred, especially upon contact with other materials,
- the operating speed is low.

It is also known to apply an inscription technique by means of a movably guided laser beam utilizing toners, wherein the toner is thermally fixed, for example, on paper; however, toner adheres only insufficiently to most polymer supports.

Furthermore, it is known to employ an inscription technique by means of a movably guided laser beam, for example, on a metal substrate, especially on a light metal substrate. Here, by way of punctually extremely intensive light emission, the laser beam produces temperatures so high that the crystal structure of the metal is superficially changed such that the metal adopts a different color. Laser beam appliances have also been used, for example, to apply letters or signs on electronic cables which are covered by a comparatively thick layer of plastic or rubber. Known are laser appliances for marking of cables with information by way of in-line laser marking which work with a freely programmable matrix system, this allows representation of almost any characters and symbols. Rates of up to 450 m/min are common in these lasers.

Owing to possible harmful effects of the laser beam on an inscription substrate of a thin polymer that is provided with ingredients such as adhesives, plasticizers, enhancers and active agents, and to the penetration depth of the beam, toner-free laser inscription on thin, sheet-like adhesive systems has heretofore not been made use of. With all adhesives there are fears that under the influence of high temperatures the adhesive mass will react with residual monomers, and with hot-melt adhesives it is feared that their adhesive power will be diminished under action of heat.

BRIEF SUMMARY OF THE INVENTION

Starting from the above, in a process according to the present invention, it is the object of the invention to provide operating parameters or implementing conditions for the inscription of adhesive systems of polymers with the aid of a movably guided laser beam, which operating parameters or implementing conditions are suited to securely prevent a detrimental change in the sheet-like adhesive system caused, for example, by a perforation eliminating the impermeability of the backing layer, negative changes in the backing layer and in ingredients such as adhesives, or, respectively, a thermal change in the additives such as plasticizers and enhancers or in the active agent.

DETAILED DESCRIPTION OF THE INVENTION

To achieve the object of the present invention, the present invention proposes to perform the inscription with the aid of a movably guided laser beam in such a manner that a detrimental influence on the ingredients such as adhesives, additives such as softeners, enhancers, or active substance contained in the adhesive system, due, in particular, to the heat generated by the laser beam or to perforation of the backing layer, which is impermeable to ingredients such as adhesive, active agent and/or water vapor, is avoided and that to this end the intensity and penetration depth of the laser beam is adjusted, in accordance with the properties of the material of the sheet-like adhesive system, in such a way that the laser beam does not penetrate far enough to reach components such as, for example, an additive—or active agent containing layer, of the sheet-like adhesive system/plaster, and, in particular, does not reach the active substance reservoir.

The inscription can also be carried out by negative signs, that is by working letters and signs from surfaces which are not affected by the laser beam. Advantageously, it is further provided that the inscription is performed immediately following the manufacture of the broad backing layer film webs, or in any later manufacturing step—after coating, adding other films by laminating, cutting into narrow rolls, or after separating as the last operational step. Here it is possible also to cover any desired working widths, i.e. including broad webs of adhesive films, by arranging several inscription units next to each other, offset, or phased.

One advantageous embodiment of the process provides that the material layer to be inscribed be covered with an overlying layer, e.g. with a color layer, which is selected such that it disintegrates already at comparatively moderate laser irradiation and in the process visualizes the lased characteristics on the background of the underlying material layer. In this way it is possible to produce a type which is particularly rich in contrast and facilitates recognition of the characters, by employing a minimum of laser energy. The optical effect can be even enhanced here by providing the overlying layer with a color which is conspicuous compared to the material layer to be inscribed.

A further advantageous embodiment of the process is characterized in that the parameters determining the intensity of the effect of the laser beam on the material layer to be inscribed, such as the irradiation energy and rate-dependent duration of action of the laser beam, are matched in such a manner that only the uppermost material layers are modified and that in the further substrate layers no changes are caused. More particularly, this measure prevents impermissible perforation of the backing layer of the sheet-like adhesive systems/plasters, and harmful effects on ingredients such as adhesives, additives and possibly active agents are avoided.

A further embodiment of the process according to the invention which is essential to the invention provides that the laser beam is guided by means of electromagnetic control such that it is possible at any time to input or amend individual signs or groups of characters according to a program of a central control unit, and, in particular, to input characters by hand via an EDP-controlled type-writer-like keyset ("keyboard"). With the present invention it is for the first time possible to manually input characters and data records in a sheet-like adhesive system/plaster as with a typewriter, which is of particular advantage.

Finally, the process according to the invention provides that to produce a single-colored or multicolored pattern of characters or signs, at least two pigmented layer are disposed on the inscription substrate layer so as to overly one another, and that these are disintegrated by extremely accurate penetration depth control of the laser beam in such a way that the respective underlying pigmented color layer is visible.

This manner of inscription could also be carried out on an appropriate polymer background. Altogether, the process according to the invention overcomes the attitude hitherto held by the experts that a sheet-like adhesive system/plaster can not be utilized for inscription by means of a laser beam because of the sensitivity of the ingredients such as adhesives, additives and active agents, and the depth action of a laser beam. This prejudice is out-dated by the invention since through the invention it has now become possible to control the laser beam, respectively its intensity, in such a way that it affects only the uppermost material layers and apart from that has no effect on the remaining substrate.

The process according to the invention now dispels the reservations against laser inscription of sheet-like adhesive systems, which have hitherto stood in the way of utilizing laser inscription in this sector. It emerges that laser inscription is useful, accurate, can be modified without a need to invest time and is adaptable to any application case.

The advantages of the laser inscription according to the process of the present invention are:

- by way of the contact-free inscription it is advantageously avoided to exert pressure on a sheet-like adhesive system/plaster,
- the process is characterized by high rates,
- the flexibility of the inscription process permits the exchange and the utilization of any desired characters and data records without time delay,
- the precision of the inscription enables the application of machine-readable markings, computer-suitable numerals, barcodes or similar signs, which come up to the usual diversity of information,
- it can be utilized in an extremely flexible manner in the various production steps,
- it can also be used on broad adhesive film webs, which is especially profitable.

The invention is uncomplicated and useful and presents an optimal solution to the task set at the beginning.

The process can be realized by a suitable device, namely a device for inscription of a sheet-like adhesive system, in particular for realizing the process according to the invention, comprising a laser applicant which cooperates with means for the control of the laser beam as to its direction and irradiation intensity in accordance with a control unit which is provided with a data memory and date processor and whose program

- is controlled either by data from other production steps or
- by the fact that a keyboard with a converter for immediate manual digital input of characters or other signs or corresponding data records is superimposed on the control unit, so that intervention in an inscription programme is possible at any time and any desired data or data records can be manually inputted, or
- by data from other production steps or manually.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

What is claimed is:

1. A method of using a toner-free process for inscription of a sheet-like active agent-containing therapeutic system having an adhesive side and an adhesive-free side, said system comprising at least one active ingredient-containing layer, a material layer to be inscribed, and a backing layer impermeable to ingredients or water vapor, by using a movably guided laser beam emission device, said process comprising:

placing the sheet-like active agent-containing system with the adhesive side facing a support position;

guiding the laser emission device to emit the laser beam onto the sheet-like active agent-containing therapeutic system by a program of a manually operable central control unit; and controlling the intensity and penetration depth of the laser beam according to the material properties of said sheet-like active agent-containing system in such a way that the laser beam does not penetrate far enough to reach one of the at least one active ingredient-containing layer and preventing a detrimental influence on the ingredients contained in the system.

2. The method according to claim 1 wherein the active-agent containing therapeutic system is in the form of a plaster.

3. The method according to claim 1 wherein said detrimental influence is heat generated by said guided laser beam.

4. The method according to claim 1 wherein said detrimental influence is a perforation of said backing layer.

5. The method according to claim 1 and further including covering the layer to be inscribed with an overlying layer having information in the form of characters or signs thereon, said overlying layer being a color layer which disintegrates at a moderate laser irradiation level, applying the moderate laser irradiation level to disintegrate the color level and thereby inscribing the laser-exposed information in the form of characters or signs on the underlying layer to be inscribed.

6. The method according to claim 1 wherein at least one pigment-containing layer is under the layer to be inscribed and each of the at least one pigment-containing layers disintegrates at a moderate laser irradiation level, and the process further includes applying the moderate laser irradiation level to disintegrate the at least one pigment containing layer while forming the laser-exposed character onto the underlying pigmented layer.

7. The method according to claim 1 wherein the overlying information layer has a conspicuous color relative to the layer to be inscribed.

8. The method according to claim 1 and further including setting the intensity of the effect of the laser beam to particular parameters, and setting the parameters determining the intensity of the effect of the laser beam on the layer to be inscribed to modify only the uppermost layers of the system.

9. The method according to claim 1 and further including guiding by electromagnetic control the movably guided laser beam to amend, delete or input at any point the information being inscribed by the program of the manually operable central control unit.

10. The method according to claim 9 wherein the central control unit includes a keyboard.

11. A method according to claim 9 and further including transferring the information to the program of the central control unit.

12. A method according to claim 1 wherein the process further includes a method to produce single-colored or multi-colored pattern of characters or signs comprising applying at least two overlying pigmented layers to the layer to be inscribed, and further including disintegrating the at least two pigmented layers by accurate control of the penetration depth of the laser beam to visualize the at least two underlying pigmented color layers.

* * * * *